United States Patent
Nathwani et al.

(10) Patent No.: US 10,426,845 B2
(45) Date of Patent: Oct. 1, 2019

(54) DIABETES GENE THERAPY

(71) Applicant: UCL Business PLC, London (GB)

(72) Inventors: Amit Nathwani, London (GB); Maria Notaridou, London (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 15/764,742

(22) PCT Filed: Sep. 30, 2016

(86) PCT No.: PCT/GB2016/053057
§ 371 (c)(1),
(2) Date: Mar. 29, 2018

(87) PCT Pub. No.: WO2017/055872
PCT Pub. Date: Apr. 6, 2017

(65) Prior Publication Data
US 2018/0272006 A1     Sep. 27, 2018

(30) Foreign Application Priority Data
Sep. 30, 2015 (GB) .................................. 1517329.7

(51) Int. Cl.
*A61K 48/00* (2006.01)
*A61K 38/28* (2006.01)
*A61P 3/10* (2006.01)
*C07K 14/62* (2006.01)

(52) U.S. Cl.
CPC .......... *A61K 48/0066* (2013.01); *A61K 38/28* (2013.01); *A61K 48/0058* (2013.01); *A61P 3/10* (2018.01); *C07K 14/62* (2013.01); *C12N 2750/14143* (2013.01)

(58) Field of Classification Search
CPC ........ A61K 48/0066; A61K 31/28; A61P 3/10
See application file for complete search history.

(56) References Cited

U.S. PATENT DOCUMENTS

2007/0243167 A1* 10/2007 Brown ............... A61K 48/0066 424/93.2
2015/0133530 A1     5/2015 Srivastava et al.

FOREIGN PATENT DOCUMENTS

| WO | WO-2005097981 A2 * | 10/2005 | ......... A61K 48/0066 |
| WO | 2005/097981 A3 | 3/2006 | |
| WO | 2011/005968 A1 | 1/2011 | |
| WO | WO-2011005968 A1 * | 1/2011 | .......... C07K 14/755 |
| WO | 2015/012924 A2 | 1/2015 | |
| WO | WO-2015012924 A2 * | 1/2015 | ............. C12N 15/85 |

OTHER PUBLICATIONS

Gan Shu Uin et al., "Correction of Murine Diabetic Hyperglcaemia With a Single Systemic Administration of an AAV2/8 Vector Containing a Novel Codon Optimized Human Insulin Gene.," Current Gene Therapy 2016, vol. 16, No. 1, Feb. 2016, pp. 65-72, XP002764798.
Notardiou M. et al., "Correction of murine diabetic hyperglycaemia with a single systemic administration of an AAV8 vector containing a novel codon optimized human insulin gene", Human Gene Therapy 2016, vol. 26, No. 10, Oct. 2015, p. A67, Abstract P135 for Presentation given at Collaborative Congress of the European-Society-Of-Gene-And-Cell-Therapy (ESGCT) and Finnish-Society-; Helisnki, Finland; Sep. 17-20, 2015.
Jul. 7, 2016—GB Search Report of GB1517329.7.
Ward et al., "Codon optimization of human factor VIII cDNAs leads to high-level expression", Blood, vol. 117, No. 3, Jan. 20, 2011, pp. 798-807, electronically published Nov. 1, 2010.
Dec. 6, 2016—International Search Report of PCT/GB2016/053057.
Woo et al., "AAV Mediated Human Insulin Gene Expression in Liver of Diabetic Rats", Molecular Therapy, Nature Publishing Group, GB, vol. 9, May 1, 2004, pp. 244.

* cited by examiner

*Primary Examiner* — Antonio Galisteo Gonzalez
(74) *Attorney, Agent, or Firm* — Banner & Witcoff, Ltd.

(57) ABSTRACT

There is described a nucleic acid molecule comprising a nucleotide sequence encoding for a functional preproinsulin protein wherein the nucleotide sequence has at least 86% identity to the sequence of SEQ ID NO. 1. Also described are: vectors comprising the nucleic acid molecule for expressing the preproinsulin protein; host cells comprising the nucleic acid molecule or a vector; a transgenic animal comprising cells comprising the nucleic acid molecule or the vector; a pharmaceutical composition comprising the nucleic acid molecule or the vector; a method of treating diabetes comprising administering a therapeutically effective amount of the vector to a patient suffering from diabetes; the nucleic acid molecule for use in therapy; and the nucleic acid molecule or the vector for use in the treatment of diabetes.

Figure 1:
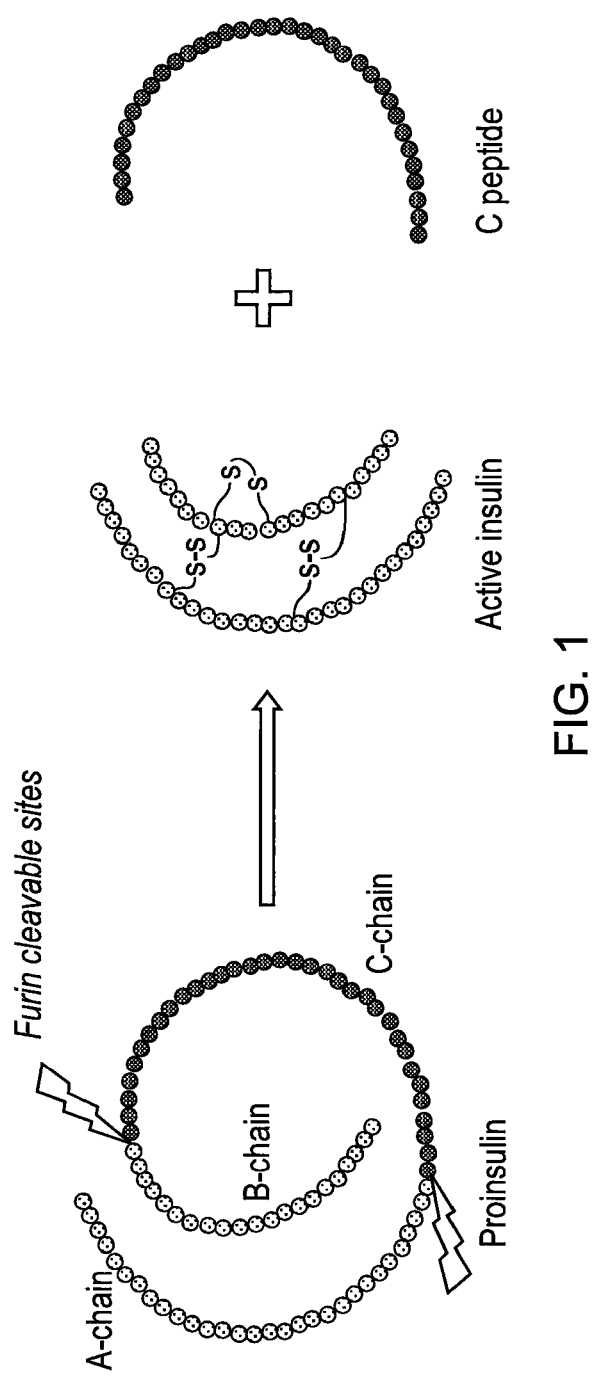

16 Claims, 7 Drawing Sheets
Specification includes a Sequence Listing.

DIABETES GENE THERAPY

FIELD OF THE INVENTION

The invention relates to a new gene therapy approach for treating diabetes. In particular, this approach involves the use of a novel codon optimised human insulin gene. Therefore, the invention relates to this new gene sequence, vectors comprising the gene sequence and methods involving use of the sequence.

BACKGROUND TO THE INVENTION

Diabetes is a lifelong metabolic disorder that affects 3.2 million people in the UK and over 347 million people worldwide. It is a leading cause of death with 1.5 million deaths annually. More than 80% of diabetes deaths occur in low- and middle-income countries. Approximately £10 billion is spent by the NHS on diabetes annually, which is almost 10 percent of the entire NHS budget.

Diabetes is a chronic disease in concomitant with severe secondary complications, mainly caused by poor glycaemia control. Actual treatment with exogenous insulin often fails to prevent and control these complications, leading to significant morbidity and mortality.

Diabetes mellitus is usually classified as type 1 or type 2 diabetes. The former results from failure and/or destruction of the insulin-producing (3-cells in the pancreas, often due to an autoimmune response. In contrast, type 2 is characterized by insulin resistance usually combined with an insulin secretory defect. Both forms of diabetes are characterised by hyperglycaemia which if not controlled adequately can lead to serious long-term complications including cardiovascular disease, stroke, kidney failure, foot ulcers and damage to the eyes. Current treatment of diabetes is aimed at lowering blood glucose levels with insulin the main stay of treatment for type I diabetes and combination of biguanides and sulphonylureas with or without insulin being used for type II diabetes. This treatment is highly demanding, invasive, expensive and not curative. In addition, relatively few patients truly achieve a normo-glycaemic state, though this is changing with the use of insulin infusion pumps, regulated by glucose sensing devices, where this is available and affordable.

Gene therapy offers the potential of a cure through continuous, endogenous production of insulin following a single therapeutic manoeuvre. Type I diabetes is well suited to somatic gene transfer approaches as it arises from a defect in a single protein, Insulin. Additionally, ectopic expression of functional human insulin has been demonstrated in a variety of different settings.

There have been many attempts at experimental gene and stem cell therapy to treat diabetes. However, the majority involve complicated protocols and ex-vivo cell manipulations, followed by transplantation of transfected or trans-differentiated cells to the diabetic animals. In vivo direct gene therapy is theoretically attractive by eliminating in vitro stages with the attendant risks of infection and failure of the gene transfected cell transplants to survive and develop an adequate blood supply.

The liver, with its embryological origins in primitive endoderm similar to the pancreas and the important role it plays in glucose homeostasis, has been considered as a suitable site to synthesize insulin. Amongst vectors available for gene therapy, there has been considerable interest in adeno-associated viral vectors (AAV) in part due to their excellent safety profile. These vectors, when pseudotyped with serotype 8 capsid (AAV8), have shown a remarkable tropism for the liver. Unlike other viral vectors, e.g. adenovirus and poxvirus, the prevalence of neutralizing antibodies to AAV8 in humans is low, enabling effective transduction of the liver following a simple systemic injection of AAV8, as illustrated in patients with severe haemophilia B (Nathwani, et al 2011). In 2011, Nathwani and colleagues reported that a single injection of AAV8-Factor IX in clinical treatment of patients with Hemophilia B had encouraging long-lasting therapeutic effects.

Gene therapy for diabetes could be facilitated by the development of a small expression cassette driven by a liver specific promoter driving the furin cleavable human proinsulin gene.

Insulin is synthesized as part of a 11.5 kDa precursor protein called pro-insulin. Pro-insulin is packaged into secretory vesicles where it is processed into mature insulin (6 kDa).

WO 2005/097981 discloses a herpes simplex viral vector which may contain a nucleotide sequence encoding insulin. However, this nucleotide sequence is the wild type sequence and does not provide particularly high levels of expression.

SUMMARY OF THE INVENTION

The inventors have surprisingly found that a novel codon optimised insulin sequence results in at least 10 fold increase in insulin production in cells transduced with that sequence compared to the wild type insulin gene (INS gene).

Therefore, in a first aspect of the invention, there is provided a nucleic acid molecule comprising a nucleotide sequence encoding a functional preproinsulin protein wherein the nucleotide sequence has at least 86% identity to the sequence of SEQ ID NO. 1.

The nucleotide sequence has at least 86% identity to the sequence of SEQ ID NO. 1. In some embodiments, the nucleotide sequence has at least 87% identity to the sequence of SEQ ID NO. 1. In other embodiments, the nucleotide sequence has at least 88% identity to the sequence of SEQ ID NO. 1.

In a particularly preferred embodiment, the nucleotide sequence has at least 89% identity to the sequence of SEQ ID NO. 1. In this regard, the invention provides a nucleic acid molecule comprising a nucleotide sequence encoding a functional preproinsulin protein wherein the nucleotide sequence has at least 89% identity to the sequence of SEQ ID NO. 1.

In further embodiments, the nucleotide sequence has at least 90% identity to the sequence of SEQ ID NO. 1. In some embodiments, the nucleotide sequence has at least 91% identity to the sequence of SEQ ID NO. 1. In other embodiments, the nucleotide sequence has at least 92% identity to the sequence of SEQ ID NO. 1. In particular embodiments, the nucleotide sequence has at least 93% identity to the sequence of SEQ ID NO. 1. In further embodiments, the nucleotide sequence has at least 94% identity to the sequence of SEQ ID NO. 1. In some embodiments, the nucleotide sequence has at least 95% identity to the sequence of SEQ ID NO. 1. In other embodiments, the nucleotide sequence has at least 96% identity to the sequence of SEQ ID NO. 1. In particular embodiments, the nucleotide sequence has at least 97% identity to the sequence of SEQ ID NO. 1. In further embodiments, the nucleotide sequence has at least 98% identity to the sequence of SEQ ID NO. 1. In some embodiments, the nucleotide sequence has at least 99% identity to the sequence of SEQ ID NO. 1. In other embodiments, the nucleotide sequence has at least 99.5% identity to the sequence of SEQ ID NO. 1. In particular embodiment, the nucleotide sequence has the sequence of SEQ ID NO. 1.

The nucleotide sequence encodes a functional preproinsulin protein. A functional preproinsulin protein is one which can be processed in a cell into biologically active insulin. A functional preproinsulin protein can be processed into proinsulin and then into biologically active insulin.

Preproinsulin is a biologically inactive precursor to the biologically active insulin. Preproinsulin contains a 24-residue signal peptide which directs the nascent polypeptide chain to the rough endoplasmic reticulum (RER). The signal peptide is cleaved as the polypeptide is translocated into the lumen of the RER, forming proinsulin. In the RER, the proinsulin folds into the correct conformation and 3 disulfide bonds are formed. It is then transported to the Golgi apparatus where it is packaged into secretory vesicles, and where it is processed by a series of proteases such as furin to form mature active insulin. Mature insulin has 35 fewer amino acids; 4 are removed altogether, and the remaining 31 form the C-peptide. The C-peptide is abstracted from the centre of the proinsulin sequence; the two other ends (the A chain and B chain) remain connected by disulfide bonds and form the active insulin molecule (see FIG. 1 below).

C peptide is extensively used to measure insulin in the blood as it is more stable that active insulin and therefore provides a better representation of the insulin amounts released (Callej as et al, 2013, Ren et al, 2007).

In preferred embodiments, the nucleotide sequence encodes for human preproinsulin. This can be processed into human insulin. More preferably, the nucleotide sequence encodes for a preproinsulin protein having the amino acid sequence of SEQ ID NO. 2.

In a second aspect of the invention there is provided a vector for expressing a preproinsulin protein.

The vector comprises the nucleic acid molecule described above. This means that the vector contains a nucleotide sequence encoding for a functional preproinsulin protein so that when this sequence is expressed, a functional preproinsulin protein is produced by the cell in which the vector is contained. This can then be processed into proinsulin which can be converted into active insulin.

The sequence of SEQ ID NO. 1 is a codon optimised version of the coding sequence of the insulin (INS) gene. This sequence has not been codon optimised in a normal way. Instead, the codons have been selected based on the codons used for proteins which are expressed at a high level in the liver. The reason for this is that the vector is normally expressed in the liver. This special codon optimisation process has been found to produce a nucleotide sequence which gives surprisingly high expression. The sequence of SEQ ID NO. 1 has 85% identity to the wild type sequence.

The nucleotide sequence encoding for a preproinsulin protein is preferably between 300 and 400 nucleotides in length. In some embodiments, the nucleotide sequence encoding for a functional preproinsulin protein is between 320 and 350 nucleotides in length. In other embodiments, the nucleotide sequence encoding for a functional preproinsulin protein is between 330 and 340 nucleotides in length. In particular embodiments, the nucleotide sequence encoding for a functional preproinsulin protein is about 333 nucleotides in length.

Preferably the vector further comprises a promoter. The promoter causes expression of the nucleotide sequence encoding for a functional preproinsulin protein. Any appropriate promoter may be used, such as HLP, LP1, HCR-hAAT, ApoE-hAAT, and LSP. These promoters are described in more detail in the following references: HLP: McIntosh J. et al., Blood 2013 Apr. 25, 121(17):3335-44; LP1: Nathwani et al., Blood. 2006 Apr. 1, 107(7): 2653-2661; HCR-hAAT: Miao et al., Mol Ther. 2000; 1: 522-532; ApoE-hAAT: Okuyama et al., Human Gene Therapy, 7, 637-645 (1996); and LSP: Wang et al., Proc Natl Acad Sci USA. 1999 Mar. 30, 96(7): 3906-3910. A preferred promoter is also described in WO 2011/005968. Preferably, the promoter is a liver specific promoter. In particular embodiments, the promoter is an HLP promoter.

The vector may be any appropriate vector for expressing the preproinsulin protein, including viral and non-viral vectors. Viral vectors include a parvovirus, an adenovirus, a retrovirus, a lentivirus or a herpes simplex virus. The parvovirus may be an adenovirus-associated virus (AAV). The vector is preferably a recombinant adeno-associated viral (rAAV) vector or a lentiviral vector. More preferably, the vector is a rAAV vector.

The vector of the invention, when used in gene therapy treatment, can provide continuous long-term endogenous expression of human insulin following a single peripheral vein administration of vector encoding the gene for human insulin into patients with diabetes, e.g. type I diabetes. It has been found that the codon optimised insulin sequence results in at least 10 fold increase in insulin production in cells transduced with the sequence compared with the wild type sequence.

The advantages of this gene transfer approach with the codon optimised insulin sequence are:

1. A single peripheral vein infusion of vector encoding codop-hINS resulting in long-term endogenous expression of human insulin in patients with type I diabetes. Stable long-term expression of insulin following gene transfer will:
   a. exert more pronounced clinic benefit than possible with regular insulin injections, thereby improving the prospects of preventing end organ damage and life expectancy;
   b. eliminate the need for regular life-long injections of insulin thus improving quality of life; and
   c. result in a potential saving to the NHS from a reduction/elimination of chronic effects of poor diabetic control which is difficult to achieve in >70% of patients,
2. More potent expression from the codon optimised expression cassette resulting in therapeutic benefit using lower doses of vector;
3. Continuous plasma levels of insulin following gene transfer improve the prospects of correcting pathology especially damage to the peripheral nerves;
4. Expression of insulin from the liver will reduce the risk of developing neutralising antibodies to this protein.

A vector according to the invention may be a gene delivery vector. Such a gene delivery vector may be a viral gene delivery vector or a non-viral gene delivery vector.

Accordingly, the present invention provides gene delivery vectors based on animal parvoviruses, in particular dependoviruses such as infectious human or simian AAV, and the components thereof (e.g., an animal parvovirus genome) for use as vectors for introduction and/or expression of a preproinsulin protein in a mammalian cell. The term "parvoviral" as used herein thus encompasses dependoviruses such as any type of AAV.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience, the present invention is further exemplified and described herein by reference to AAV. It is, however, understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

In an AAV suitable for use as a gene therapy vector, the vector genome typically comprises a nucleic acid to be packaged for delivery to a target cell. According to this particular embodiment, the heterologous nucleotide sequence is located between the viral ITRs at either end of the vector genome. In further preferred embodiments, the parvovirus (e.g. AAV) cap genes and parvovirus (e.g. AAV) rep genes are deleted from the template genome (and thus from the virion DNA produced therefrom). This configuration maximizes the size of the nucleic acid sequence(s) that can be carried by the parvovirus capsid.

According to this particular embodiment, the nucleic acid is located between the viral ITRs at either end of the substrate. It is possible for a parvoviral genome to function with only one ITR. Thus, in a gene therapy vector of the invention based on a parvovirus, the vector genome is flanked by at least one ITR, but, more typically, by two AAV ITRs (generally with one either side of the vector genome, i.e. one at the 5' end and one at the 3' end). There may be intervening sequences between the nucleic acid in the vector genome and one or more of the ITRs.

Preferably, the nucleotide sequence encoding a functional preproinsulin protein (for expression in the mammalian cell) will be incorporated into a parvoviral genome located between two regular ITRs or located on either side of an ITR engineered with two D regions.

AAV sequences that may be used in the present invention for the production of AAV gene therapy vectors can be derived from the genome of any AAV serotype.

Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini et al, 1997; Srivastava et al, 1983; Chiorini et al, 1999; Rutledge et al, 1998; and Wu et al, 2000. AAV serotype 1, 2, 3, 4, 5, 6, 7, 8 or 9 may be used in the present invention. However, AAV serotypes 1, 5 or 8 are preferred sources of AAV sequences for use in the context of the present invention. In some embodiments, serotype 8 is preferred. The sequences from the AAV serotypes may be mutated or engineered when being used in the production of gene therapy vectors.

Preferably, the AAV ITR sequences for use in the context of the present invention are derived from AAV1, AAV2, AAV4 and/or AAV6. Likewise, the Rep (Rep78 and Rep52) coding sequences are preferably derived from AAV1, AAV2, AAV4 and/or AAV6. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al, 1999). Moreover, the Rep sequences and ITRs of many AAV serotypes are known to efficiently cross-complement (i.e., functionally substitute) corresponding sequences from other serotypes in production of AAV particles in mammalian cells. US 2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped AAV particles comprising the capsid proteins of a serotype (e.g., AAV1, 5 or 8) and the Rep and/or ITR sequences of another AAV serotype (e.g., AAV2). Such pseudotyped rAAV particles are a part of the present invention.

Modified "AAV" sequences also can be used in the context of the present invention, e.g. for the production of AAV gene therapy vectors. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of AAV5 or pseudotyped AAV5 vectors. For example, the start codon of the Rep sequences can be modified, VP splice sites can be modified or eliminated, and/or the VP1 start codon and nearby nucleotides can be modified to improve the production of AAV5 vectors.

Thus, the viral capsid used in the invention may be from any parvovirus, either an autonomous parvovirus or dependovirus, as described above. Preferably, the viral capsid is an AAV capsid (e.g., AAV1, AAV2, AAV3, AAV4, AAV5 or AAV6 capsid). In general, the AAV1 capsid or AAV6 capsid are preferred. The choice of parvovirus capsid may be based on a number of considerations as known in the art, e.g., the target cell type, the desired level of expression, the nature of the heterologous nucleotide sequence to be expressed, issues related to viral production, and the like. For example, the AAV1 and AAV6 capsid may be advantageously employed for skeletal muscle; AAV1, AAV5 and AAV8 for the liver and cells of the central nervous system (e.g., brain); AAV5 for cells in the airway and lung or brain; AAV3 for bone marrow cells; and AAV4 for particular cells in the brain (e.g., appendable cells).

It is within the technical skills of the skilled person to select the most appropriate virus, virus subtype or virus serotype. Some subtypes or serotypes may be more appropriate than others for a certain type of tissue.

For example, liver-specific expression of a nucleic acid of the invention may advantageously be induced by AAV-mediated transduction of liver cells. Liver is amenable to AAV-mediated transduction, and different serotypes may be used (for example, AAV1, AAV5 or AAV8). In some embodiments, AAV8 is preferred. Transduction of muscle may be accomplished by administration of an AAV encoding a nucleic acid via the blood stream. Thus, intravenous or intra-arterial administration is applicable.

A parvovirus gene therapy vector prepared according to the invention may be a "hybrid" particle in which the viral TRs and viral capsid are from different parvoviruses. Preferably, the viral TRs and capsid are from different serotypes of AAV. Likewise, the parvovirus may have a "chimeric" capsid (e. g., containing sequences from different parvoviruses, preferably different AAV serotypes) or a "targeted" capsid (e. g., a directed tropism).

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans-acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. A parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a parvoviral (AAV) vector that is unable to further propagate after initial introduction into a cell. Such a safety mechanism for limiting undesirable vector propagation in a recipient may be provided by using AAV with a chimeric ITR as described in US 2003148506.

Those skilled in the art will appreciate that the viral Rep protein(s) used for producing an AAV vector of the invention may be selected with consideration for the source of the viral ITRs. For example, the AAV5 ITR typically interacts more efficiently with the AAV5 Rep protein, although it is not necessary that the serotype of ITR and Rep protein(s) are matched.

The ITR(s) used in the invention are typically functional, i.e. they may be fully resolvable and are preferably AAV sequences, with serotypes 1, 2, 3, 4, 5 or 6 being preferred. Resolvable AAV ITRs according to the present invention need not have a wild-type ITR sequence (e. g., a wild-type sequence may be altered by insertion, deletion, truncation or missense mutations), as long as the ITR mediates the desired functions, e. g., virus packaging, integration, and/or provirus rescue, and the like.

Advantageously, by using a gene therapy vector as compared with previous approaches, the restoration of protein synthesis, i.e. insulin synthesis, is a characteristic that the transduced cells acquire permanently or for a sustained period of time, thus avoiding the need for continuous administration to achieve a therapeutic effect.

Accordingly, the vectors of the invention therefore represent a tool for the development of strategies for the in vivo delivery of an insulin nucleotide sequence, by engineering the nucleic acid within a gene therapy vector that efficiently transduces an appropriate cell type, such as a liver cell.

The vector may be a self-complementary vector or a single stranded vector. In some embodiments, the vector is a single stranded vector.

The vector may further comprise a poly A tail. Preferably, this is positioned downstream of the nucleotide sequence encoding for a functional preproinsulin protein.

The vector may comprise other elements to allow the functional preproinsulin protein to be expressed. Such elements are well known to a person skilled in the art.

Preferably, the nucleic acids described above are isolated.

It would be well with the capabilities of a skilled person to produce the nucleic acid molecules described above. This could be done, for example, using chemical synthesis of a given sequence.

Further, a skilled person would readily be able to determine whether a nucleic acid expresses a functional protein. Suitable methods would be apparent to those skilled in the art. For example, one suitable in vitro method involves inserting the nucleic acid into a vector, such as a lentiviral or an AAV vector, transducing host cells, such as 293T or HeLa cells, with the vector, and assaying for insulin activity. Alternatively, a suitable in vivo method involves transducing a vector containing the nucleic acid into an animal model for diabetes and assaying for functional insulin in the plasma of the animal. Further, suitable methods are described in more detail below.

The nucleic acid can be any type of nucleic acid composed of nucleotides. The nucleic acid should be able to be expressed so that a protein is produced. Preferably, the nucleic acid is DNA or RNA.

The invention also provides a host cell comprising any one of the nucleic acid molecules or vectors described above. Preferably, the vector is capable of expressing the insulin nucleotide sequence in the host. The host may be any suitable host.

As used herein, the term "host" refers to organisms and/or cells which harbour a nucleic acid molecule or a vector of the invention, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host. A host cell may be in the form of a single cell, a population of similar or different cells, for example in the form of a culture (such as a liquid culture or a culture on a solid substrate), an organism or part thereof.

A host cell according to the invention may permit the expression of a nucleic acid molecule of the invention. Thus, the host cell may be, for example, a bacterial, a yeast, an insect or a mammalian cell.

In addition, the invention provides a transgenic animal comprising cells comprising the nucleic acid molecule encoding for a functional preproinsulin protein described above or a vector described above. Preferably the animal is a non-human mammal, especially a primate. Alternatively, the animal may be a rodent, especially a mouse; or may be canine, feline, ovine or porcine.

In one aspect, the invention provides a pharmaceutical composition comprising a nucleic acid molecule or a vector of the invention and one or more pharmaceutically acceptable excipients. The one or more excipients include carriers, diluents and/or other medicinal agents, pharmaceutical agents or adjuvants, etc.

The invention also provides a method of treating diabetes, particularly type I diabetes, the method comprising administering a therapeutically effective amount of a vector as described above to a patient suffering from diabetes. Preferably, the patient is human.

When diabetes is "treated" in the above method, this means that one or more symptoms of diabetes are ameliorated. It does not mean that the symptoms of diabetes are completely remedied so that they are no longer present in the patient, although in some methods, this may be the case. The method of treating results in one or more of the symptoms of diabetes being less severe than before treatment.

A "therapeutically effective amount" refers to an amount effective, at dosages and for periods of time necessary, to achieve the desired therapeutic result, such as raising the level of insulin in a subject (so as to lead to insulin production to a level sufficient to ameliorate the symptoms of diabetes).

Delivery of a nucleic acid or vector of the invention to a host cell in vivo may result in an increase of insulin in the host, for example to a level that ameliorates one or more symptoms of diabetes.

Further, the invention provides the nucleic acid molecule encoding for a functional preproinsulin protein as described above, or a vector as described above for use in therapy, for example, in the treatment of diabetes.

In addition, the invention provides the use of the nucleic acid molecule encoding for a functional preproinsulin protein as described above or a vector as described above in the manufacture of a medicament for treating diabetes.

The invention also provides a method for delivery of a nucleotide sequence encoding a functional preproinsulin protein to a subject, which method comprises administering to the said subject a nucleic acid molecule encoding a functional preproinsulin protein as described above or a vector as described above.

In the description above, the term "identity" is used to refer to the similarity of two sequences. For the purpose of this invention, it is defined here that in order to determine the percent identity of two nucleotide sequences, the sequences are aligned for optimal comparison purposes (e.g., gaps can be introduced in the sequence of a first nucleic acid for optimal alignment with a second amino or nucleic acid sequence). The nucleotide residues at nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length. A sequence comparison is typically carried out over the entire length of the two sequences being compared.

The skilled person will be aware of the fact that several different computer programs are available to determine the identity between two sequences. For instance, a comparison of sequences and determination of percent identity between two sequences can be accomplished using a mathematical algorithm. In a preferred embodiment, the percent identity between two nucleic acid sequences is determined using the sequence alignment software Clone Manager 9 (Sci-Ed software—www.scied.com) using global DNA alignment; parameters: both strands; scoring matrix: linear (mismatch 2, OpenGap 4, ExtGap 1).

Alternatively, the percent identity between two amino acid or nucleic acid sequences can be determined using the Needleman and Wunsch (1970) algorithm which has been incorporated into the GAP program in the Accelrys GCG software package (available at www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6.

All patent and literature references cited in the present specification are hereby incorporated by reference in their entirety.

A skilled person will appreciate that all aspects of the invention, whether they relate to, for example, the nucleic acid, the vector, the host cell or the use, are equally applicable to all other aspects of the invention. In particular, aspects of the method of treatment, for example, the administration of the nucleic acid or vector, may have been described in greater detail than in some of the other aspects of the invention, for example, relating to the use of the nucleic acid or vector for treating diabetes. However, the skilled person will appreciate where more detailed information has been given for a particular aspect of the invention, this information is generally equally applicable to other aspects of the invention. Further, the skilled person will also appreciate that the description relating to the method of treatment is equally applicable to the use of the nucleic acid or vector in treating diabetes.

DETAILED DESCRIPTION OF THE INVENTION

The invention will now be described in detail by way of example only with reference to the figures in which:

FIG. 1 shows the conversion of proinsulin to active insulin. Active insulin has 35 fewer amino acids than proinsulin; 4 are removed altogether, and the remaining 31 form the C-peptide. The C-peptide is abstracted from the centre of the proinsulin sequence; the two other ends (the A chain and B chain) remain connected by disulfide bonds and form the active insulin molecule.

Figure 2:
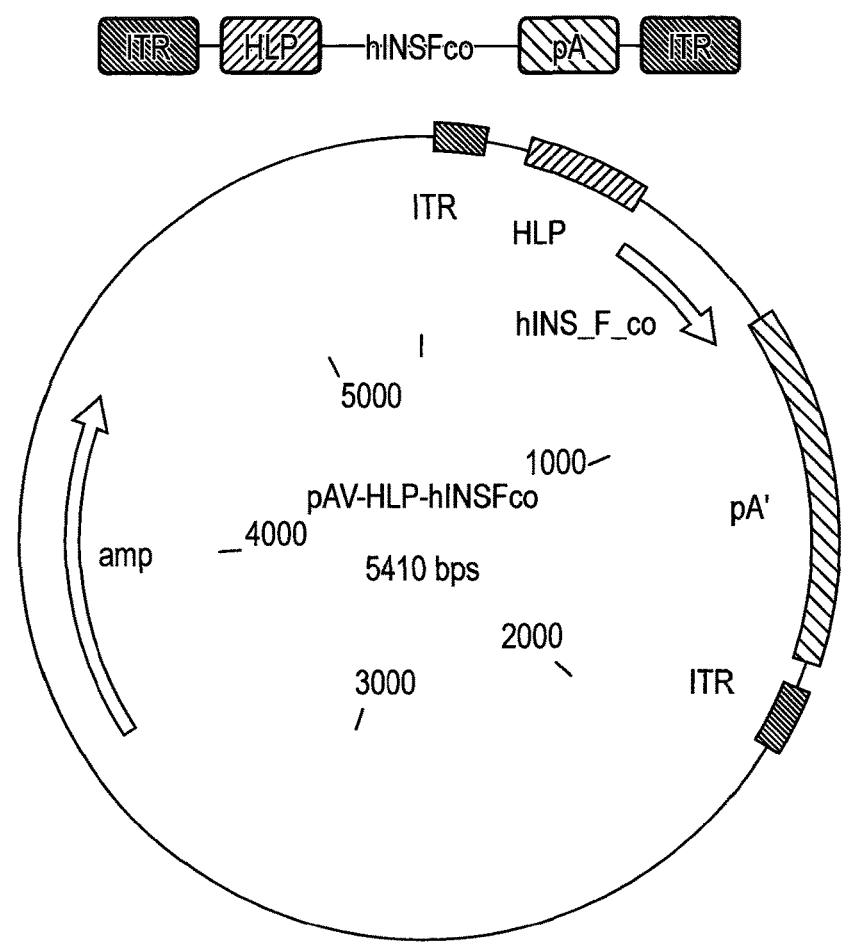

FIG. 2 is a map of the plasmid used to generate the AAV8 vector coding for the codon optimised preproinsulin of the current invention.

Figure 3:
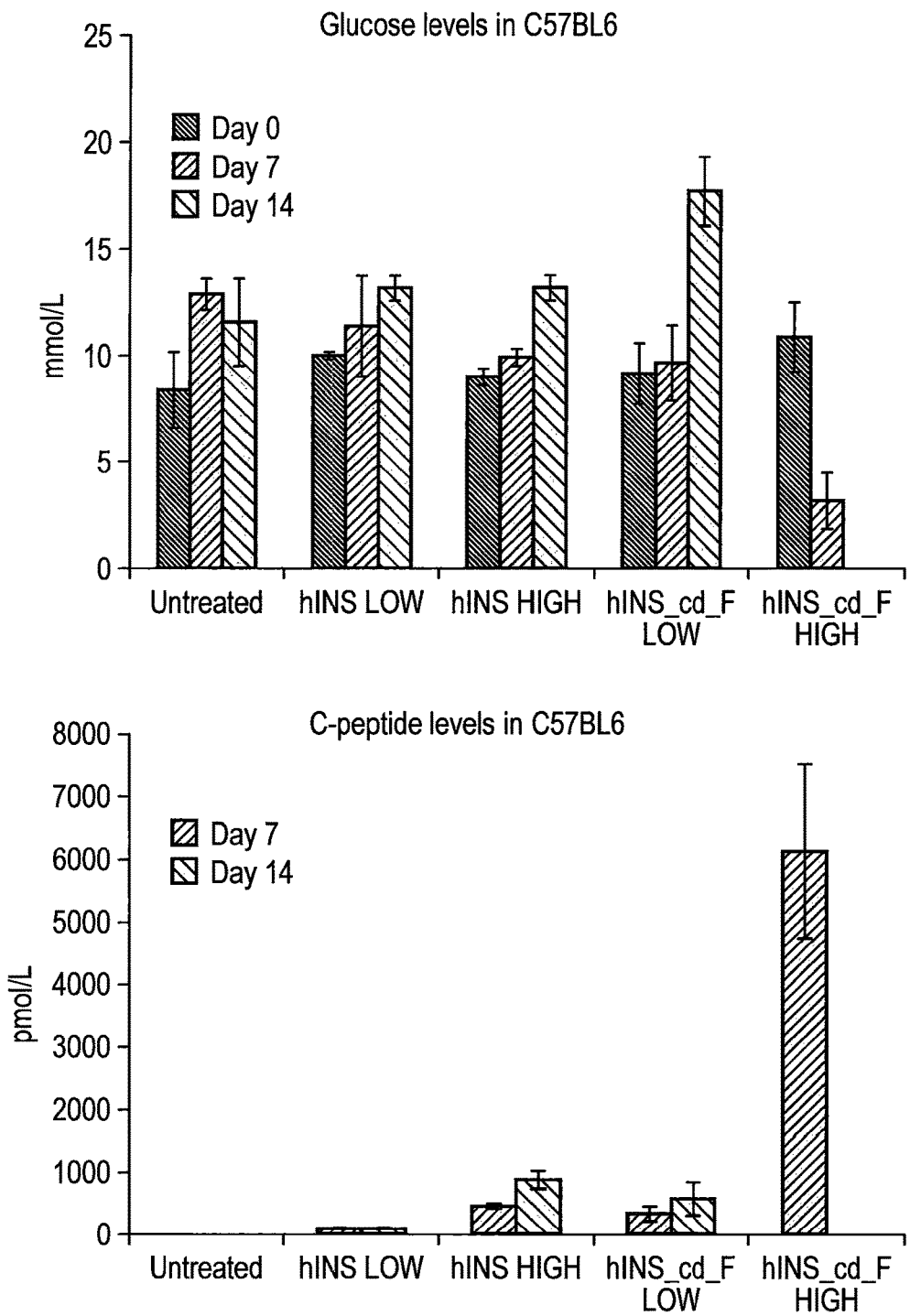

FIG. 3 shows C56BL6 data. The efficacy of rAAV-HLP-hINS and rAAV-HLP-hINSco were initially tested in C57BL6 mice in $1\times10^{10}$ (Low) and $1\times10^{11}$ (High) vg/mouse doses. Glucose levels at day 14 post injection were found significantly lower in mice transduced with rAAV-HLP-hINSco leading to hypoglyceamic events. Significant expression of insulin measured by C-peptide levels was recorded in mice transduced with both vectors.

Figure 4:
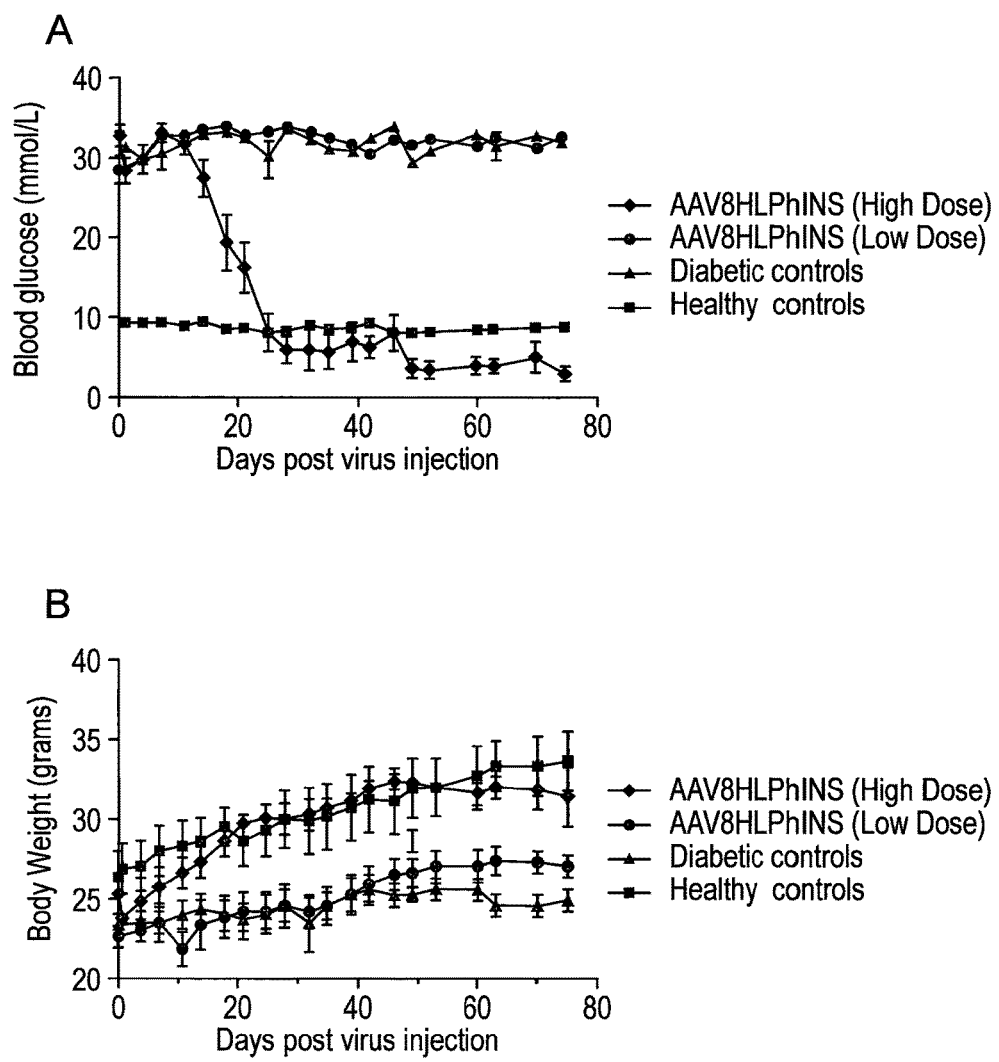
Figure 4:
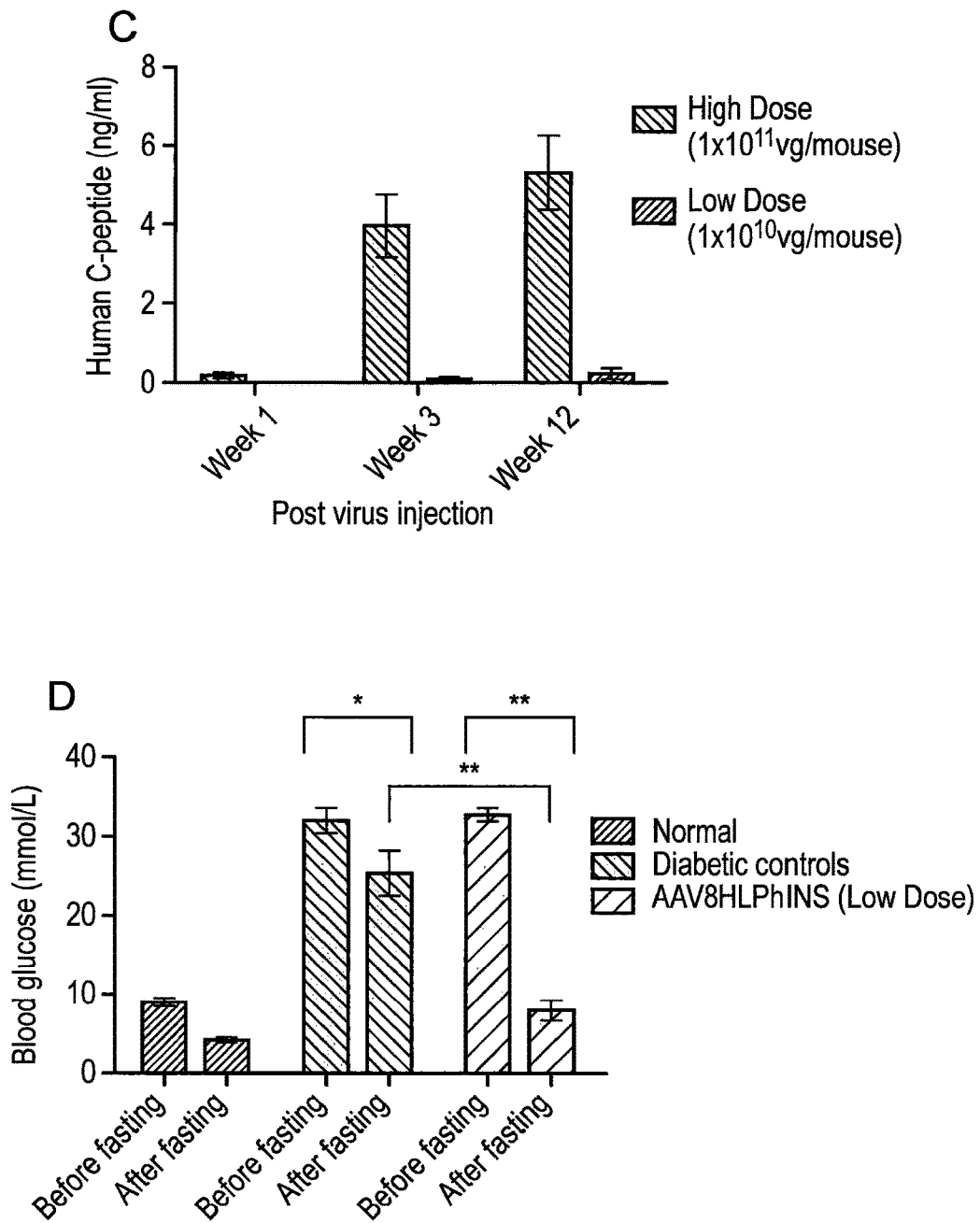

FIG. 4 shows NSG mice data. (A) Non-fasting glucose levels (B) Body weight of mice injected with $1\times10^{11}$ vg/mouse [blue], $1\times10^{10}$ vg/mouse [grey] ssAAV8-HLP-hINS virus, diabetic controls [red] and healthy controls [green]. (C) Serum human C-peptide levels measured at indicated time points post virus injection (D) Comparison of non-fasting and 16 hour fasting blood glucose levels of $1\times10^{10}$ vg/mouse dose injected AAV8-HLP-hINS (purple, n=5), diabetic (red, n=4) and healthy (green, n=4) mice, 75 days post virus injection. Data expressed as means±SE. *p=0.031, **p<0.0001.

Figure 5:
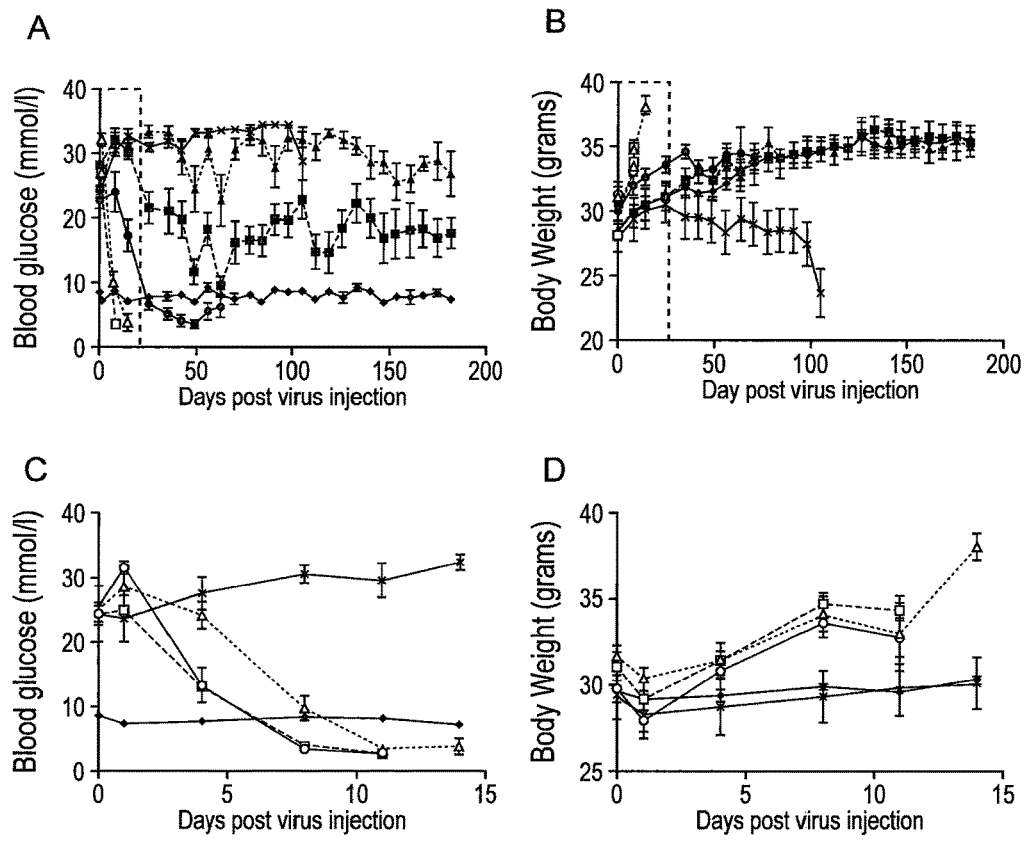
Figure 5:
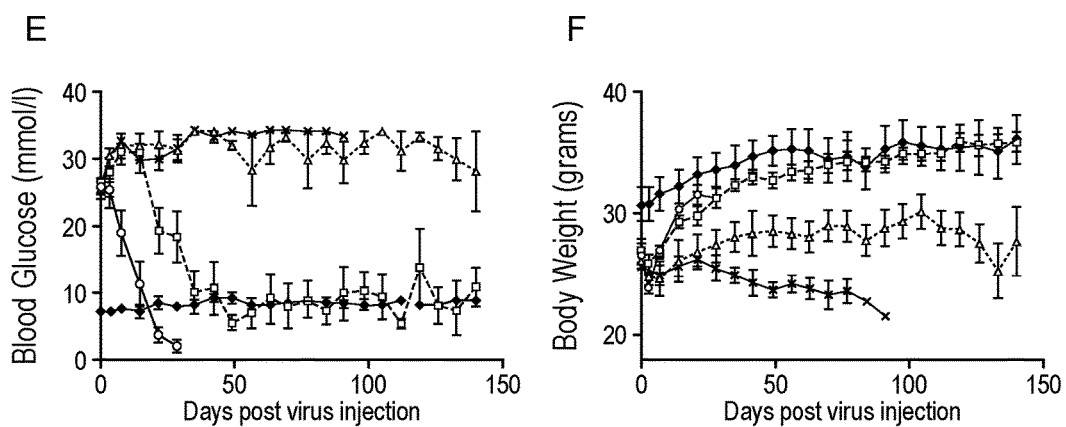

FIG. 5 shows NSG mice data. (A) Non fasting blood glucose of diabetic mice injected with high ($7.5\times10^{10}$ vg/mouse) [circles, n=5], medium ($5\times10^{10}$ vg/mouse) [squares, n=5] and low doses ($2.5\times10^{10}$ vg/mouse) [triangles, n=5] of ssAAV-HLP-hINS vector [blue] or codon optimized ssAAV-HLP-hINSco vector [purple] in comparison with healthy [green, n=4] and diabetic controls [red, n=5] (B) Body weight of diabetic mice injected with high, medium and low doses of ssAAV-HLP-hINS vector or codon optimized ssAAV-HLP-hINSco [purple] in comparison with healthy and diabetic controls. (C) Enlarged representation of the box in Figure (A) depicting the non-fasting blood glucose levels of codon optimized injected mice (D) Body weight of mice injected with codon optimized ssAAV-HLP-hINSco. (E) Separate series of experiment depicting blood glucose of mice injected with high ($1\times10^{10}$ vg/mouse) [circles, n=4], medium ($5\times10^{9}$ vg/mouse) [squares, n=4] and low ($1\times10^{9}$ vg/mouse) [triangles, n=4] of codon optimized vector AAV-HLP-hINSco. Non treated diabetic mice (red, n=4) and healthy mice (green, n=4) were included as controls. (F) Body weight of mice injected with respective doses. Results are shown as means±SE.

SUMMARY

The inventors has initially tested the efficacy of adeno-associated virus serotype 8 (AAV-8) containing the human proinsulin gene in wild type and codon optimised forms in healthy C57BL6 mice. They further report treatment of streptozotocin (STZ) diabetic immunocompromised NSG mice. A variety of doses of the wild type vector were given using one intravenous injection in diabetic NSG mice, with normal mice and untreated diabetic mice as controls. Reduction in blood sugar levels, increase in weight and general wellbeing of the animals in the higher dose ranges were observed. However, after an initial response, 10 days following injection, the animals became hypoglycemic. In the lower dose experiments, there was a slight increase in weight but no effect on non-fasting blood sugar levels.

In a second set of experiments similar to the above in NSG mice, a codon optimized human proinsulin gene was used. There was at least a ten-fold increase in insulin production for a given number of viral particles. In view of the large numbers of AAV8 viral particles that would be needed in any scaling up of this treatment for large animals, the codon optimization would appear to have considerable advantages over the non-codon optimized vector.

Materials and Methods

AAV Vectors

The human insulin wild-type DNA sequence was cloned downstream of a liver-specific HLP promoter to obtain rAAV8-HLP-hINS. The DNA sequences in rAAV8-HLP-hINS were further modified using a specially developed codon-optimization algorithm. Altogether 50 nucleotides were changed so that the codon usage profile of the resulting gene was the same as that of human albumin. The resulting 334 bp codop-hINS cDNA was 85% identical to the wild type human insulin cDNA. The codop-hINS cDNA was synthesized and cloned downstream of the HLP promoter.

Packaging, purification and titration of ssAAV8 virus rAAV-HLP-hINS and rAAV-HLP-hINSco vector particles were made by the 293T transient transfection method described before using an adenoviral helper plasmid (HGT1) and chimeric AAV2 Rep-8Cap packaging plasmid called pAAV8-2 to generate AAV8 pseudotyped vector particles (Davidoff, et al 2004, Gao, et al 2002).

Serotype 8 capsid pseudotyped vectors were purified by the previously described ion exchange chromatography method (Gao, et al 2002). Vector particles were purified, titered, and characterized as described elsewhere (Fagone, et al 2012). Gel-based titers were used for dosing of animals.

Animals

NOD.cg-PrkdcscidIl2rgtm1Wjl/SzJ (NSG) mice breeders were purchased from The Jackson Laboratory (Bar Harbor, Me., USA), bred and maintained in a specific pathogen-free facility. The breeding and experimental protocols used are in accordance with the guidelines of Institutional Animal Care and Use Committee (IACUC) of the National University of Singapore. Male NSG mice (8-12 weeks old) received a single intraperitoneal injection of 120 mg/kg STZ (Sigma-Aldrich, St Louis, Mich., USA) to induce diabetes. Body weight was measured and blood was obtained via the tail vein and placed onto test strips to measure blood glucose with an ACCU-CHEK Active glucometer (Roche Diagnostics, Indianapolis, Ill., USA). Mice with blood glucose levels of >20 mM for 4 consecutive days were considered diabetic. The ssAAV8-HLP-hINS and ssAAV8-HLP-hINSco vectors were injected via intravenous tail vein injection with specified genome copies (GC) per mouse. Blood was obtained on the indicated time points post AAV injection and at end point prior to euthanasia.

C-Peptide ELISA

The amount of C-peptide in serum sample was measured using an ELISA kit for human C-peptide (human C-peptide ELISA kit (EZHCP-20K); Millipore, Billerica, Mass.) according to the manufacturer's protocols.

Intraperitoneal Glucose Tolerance Assay (IPGTT)

The glucose tolerance test measures the clearance from the body of an intraperitoneal injected glucose load. Animals were fasted for approximately 16 hours (or indicated time), fasting blood glucose levels were determined before a solution of glucose (2 g/kg body weight; 20% w/v glucose solution, or otherwise stated) was administered by intraperitoneal (IP) injection. The group of mice injected with higher doses of AAV were not subjected to overnight fasting as the blood glucose levels were already low. They were fasted for a few hours (as indicated) before the glucose injection. Subsequently, the blood glucose level was measured at different time points (typically 7.5, 15, 30, 45 and 60 minutes). A Paired t-test was performed between treatment and control groups.

Immunohistochemical Analyses (IHC)

Liver and pancreatic tissues were excised from euthanized mice, fixed in 4% formaldehyde solution and embedded in paraffin. Antigen retrieval was performed on the 5 µm tissue sections and were incubated with anti-insulin antibody (Cat no.) at 4° C. overnight. Staining procedure was performed using Ultra-vision-One detection system (Thermo Fisher) according to the manufacturer's protocol.

Statistical Analyses

The number of animals used in each group was indicated in the respective figure legends. All values are expressed as means±SE. Statistical significance was determined by ANOVA tests, and values of $P<0.05$ were considered significant.

Results

Initial studies were designed to compare the effects of codon optimization of the human insulin coding sequence using two single stranded (ss) rAAV vectors containing either wild-type or codon-optimized insulin sequences under the control of our previously described HLP promoter (Nathwani et al, 2006). Both ssAAV-hINS expression cassettes were packaged with serotype 8 capsid using a conventional HEK293T transient transfection method, with production efficiency ($1 \times 10^4$ AAV-hFVIII particles/293T cell) being comparable to that reported previously for AAV-hFIX vectors (Nathwani et al, 2006). Assessment of viral DNA extracted from ssAAV8-HLP-codop-hINS and ssAAV5-HLP-hINS vector particles showed bands of approximately 1.8 and 3.6 kb on alkaline agarose gels, suggesting the packaging of both ss and self-complementary dimers the latter possibly spontaneously formed as AAV has the tendency to package to its maximum capacity (4 kb approximately).

Preliminary Data in C57BL6 Mice

Preliminary dose titration studies using $10^{10}$ and $10^{11}$ vg/mouse were performed to estimate the efficacy of the transduced ssAAV8-HLP-hINS in C57BL6 mice. The data showed the ability of the wild type and codon optimised insulin vectors to produce active insulin and the codon optimised insulin vector to significantly lower blood glucose levels even under the presence of endogenous insulin (FIG. 3).

Dosing of Non-Codon Optimized Vector in Diabetic NSG Mice

Preliminary dose titration studies using $10^{10}$ and $10^{11}$ vg/mouse were repeated to estimate the efficacy of the transduced ssAAV8-HLP-hINS in the diabetic mice (FIGS. 4A and B). The high dose injection resulted in gradual decrease in blood glucose levels over the first 3 weeks and the animals became hypoglycemic after 7 weeks. The low dose injected animals remained hyperglycemic under non fasting condition, but there was an increase in body weight over time compared to the control diabetics. Serum human C-peptide measurements showed no detectable human C-peptide in the control healthy and control diabetic mice, but showed a progressive increase in mice injected with $1 \times 10^{11}$ and $1 \times 10^{10}$ vg/mouse when measured at 1, 3 and 12 weeks (FIG. 4C). With food withdrawal the low-dose injected mice showed decreased blood glucose levels similar to the normal controls within 16 hours (FIG. 4D) whereas the diabetic mice continued to be hyperglycemic. The weight increase observed in the low dose treated mice, despite the hyperglycaemia, and the lowering of blood glucose after the 16 hour fasting are indications of low level insulin secretion below the threshold of our glucose detecting methods.

Comparison of Codon Optimized Versus Non-Codon Optimized Genes on In Vivo Hepatic Insulin Production in Diabetic NSG Mice.

In the second series of experiment, the doses were refined from the Series 1 experiment and the efficacies of non-codon optimized ssAAV8-HLP-hINS were compared with the codon optimized rAAV8-HLP-hINSco virus.

Non-Codon Optimized Cohorts:

Mice treated with the high dose virus ($7.5 \times 10^{10}$ vg/mouse) became hypoglycemic around 3 weeks post injection. In the medium ($5 \times 10^{10}$ vg/mouse) and low ($2.5 \times 10^{10}$ vg/mouse) dose experiments, the decrease in blood glucose levels was gradually observed at a later stage, 20-30 days after the vector injection and remained stable over the 9 month period of observation.

Mice treated with the medium dose virus ($5 \times 10^{10}$ vg/mouse) were mildly hyperglycemic and the low dose ($2.5 \times 10^{10}$ vg/mouse) remained hyperglycemic under non-fasting conditions (blue lines, FIG. 5A). The body weight of the treated mice (blue lines, FIG. 5B) became significantly higher than the diabetic controls (red line, FIG. 5B) regardless of their blood glucose levels, and close to the weight of the healthy controls (green line, FIG. 5B). The diabetic controls had to be euthanized due to the massive loss in body weight (red line). Serum was drawn from the surviving animals and human C-peptide was measured at day 140 post virus injection. The human C-peptide found in the serum of mice injected with $5 \times 10^{10}$ vg/mouse and $2.5 \times 10^{10}$ vg/mouse were 2.60±0.57 and 1.2±0.25 ng/ml respectively, which has ratios worked out to be directly proportional to the doses administered.

Codon Optimized Cohorts:

All diabetic mice injected with the 3 respective doses of codon optimized virus became hypoglycemic within 10 days (Purple lines, FIG. 5A and enlarged in FIG. 5C) and the body weight of the respective groups were reported in FIG. 5B and enlarged in FIG. 5D. There is an increase in body weight of all the groups with the decrease in blood glucose levels, We are not certain of the reason but we suspect that the mice increased in their intake of food to counter the hypoglycemic effect caused by increase in the expression of insulin over the 3 weeks. The mice either died or had to be euthanized due to the very low blood glucose levels (ranging from 2-4 mmole/L) and moribund state. We further reduced the doses of the codon optimized virus to high $1 \times 10^{10}$, medium $5 \times 10^9$ and low dose $1 \times 10^9$ vg/mouse in the third series of experiment. Non-fasting blood glucose profile and body weight are shown in FIGS. 5E and 5F respectively. Similar glucose correction to that observed by the non-codon optimized vector ssAAV8-HLP-hINS was achieved by a 10-20 fold lower dose of the codon optimized ssAAV8-HLP-hINSco.

The average human C-peptide levels obtained on Day 140 was 2.20±0.25 ng/ml in mice injected with $5\times10^9$ vg/mouse virus, and 0.36±0.09 ng/ml in mice injected with $1\times10^9$ vg/mouse virus and the ratio (6:1) is almost directly proportional to that of the two injected virus doses (5:1). The diabetic control animals were euthanized due to severe weight loss and moribund state at 90 days post injection. The mice injected with low dose appeared active and healthy despite the lower weight gain over time (FIGS. 5B and 5F) compared to the medium dose injected and healthy controls but had to be euthanized according to the IACUC guidelines for unacceptable weight loss as compared to healthy animals after 150 days.

Discussion

We report here the results of effective insulin gene therapy for STZ induced Type 1 diabetic mice using a serotype 8 pseudotyped, single stranded AAV vector containing our previously described liver specific promoter (HLP) [McIntosh et al, 2013]. The experiments reported here have two salient features:

1) The treatment consisted of only a single IV injection of an AAV8 vector with the human proinsulin gene. This AAV8-HLP vector backbone has been previously used successfully in a human clinical trial of patients suffering from Hemophilia B. All the patients in the trial showed FIX transgene expression at levels sufficient to improve the bleeding phenotype, with few side effects (Nathwani et al, 2014). The safety and therapeutic durability (i.e., up to 4 years) demonstrated by the AAV8 vector in the human clinical studies would suggest that this strategy could be of therapeutic value for some diabetic patients.

2) The codon optimization of the human proinsulin gene resulted in a 10-20 fold reduction in the vector dose required to achieve similar non fasting blood glucose levels when compared to the non-codon optimized vector. The mice injected with $5\times10^9$ vg/mouse of ssAAV8-HLP-hINS vector had similar blood glucose profiles and C-peptide secretion as the codon optimized cohort injected with $5\times10^9$ vg/mouse. The secretion of human C-peptide by the codon optimized vector is up to approximately 10 times more than the non-codon optimized vector in vivo measured at day 140 post injection. Similar codon optimization strategies were performed on human Factor VIII achieving a 29 to 44 fold increase in expression, yielding more than 200% normal Factor VIII levels (Ward et al, 2011). Treatments on hemophilia canine models and human clinical trials also showed evidence that lower AAV doses introduced are less likely to elicit immune responses (Nathwani et al, 2011, Nathwani et al, 2014). A reduced number of vector particles may lessen the risk of hepatocyte vector transaminitis damage and reduce costs of vector production. This should facilitate the production of vector in sufficient quantities to treat large animals including dogs suffering from spontaneous diabetes and human clinical trials.

We have titrated vector dosage ($10^9$-$10^{11}$ vg/mouse) leading to a spectrum of hypoglycemia to hyperglycemia when animals were fed ad libitum and have obtained doses with consistent satisfactory control of glucose homeostasis with dose selection, avoiding these extremes. In the various doses used, we have endeavored to determine the appropriate dose, $5\times10^{11}$ vg/mouse for non-codon optimized virus, and $5\times10^{10}$ vg/mouse for codon optimized virus, to approach euglycaemia or slightly hyperglycaemic on a normal diet that is not unduly disturbed by up to 8 hours of fasting. The lack of any evidence of decrease in prolonged insulin secretion for more than 9 months suggests that during this period there has not been significant gene silencing nor other mechanisms inhibiting the insulin expression, although this will need to be addressed with immune competent animals in future experiments. The weight of the treated mice with slight hyperglycaemia or euglycemia has been restored to the range of the healthy controls and remained relatively stable over the 9 month to 1 year period.

REFERENCES

1. Callejas D, et al. (2013) *Diabetes.* 62(5):1718-29.
2. Davidoff, A. M. et al. (2004). *J Virol Methods,* 121, 209-215.
3. Fagone, P. et al. (2012) *Hum Gene Ther Methods,* 23, 1-7.
4. Gao, G. P. et al. (2002) *Proc Natl Acad Sci USA,* 99, 11854-11859.
5. McIntosh, J. et al. (2013) *Blood,* 121, 3335-3344.
6. Nathwani, A. C. et al. (2006). *Blood,* 107(7), 2653-2661.
7. Nathwani, A. C. et al. (2011) *N Engl J Med,* 365, 2357-2365.
8. Nathwani A. C. et al. (2014) *N Engl J Med.* 371(21): 1994-2004.
9. Ren B. et al. *Diabetologia* 50(9): 1910-1920.
10. Ward N. J. et al. (2011) *Blood,* 117(3):798-807.

The invention claimed is:

1. A nucleic acid molecule comprising a nucleotide sequence encoding a functional preproinsulin protein wherein the nucleotide sequence has at least 89% identity to the sequence of SEQ ID NO. 1.

2. The nucleic acid molecule of claim 1, wherein the nucleotide sequence has at least 95% identity to the sequence of SEQ ID NO. 1.

3. The nucleic acid molecule of claim 1, wherein the nucleotide sequence has at least 98% identity to the sequence of SEQ ID NO. 1.

4. The nucleic acid molecule of claim 1, wherein the nucleotide sequence has the sequence of SEQ ID NO. 1.

5. The nucleic acid molecule of claim 1, wherein the nucleotide sequence encodes human preproinsulin.

6. The nucleic acid molecule of claim 1, wherein the nucleotide sequence encodes a preproinsulin protein having the amino acid sequence of SEQ ID NO. 2.

7. A vector for expressing preproinsulin protein, the vector comprising the nucleic acid molecule of claim 1.

8. The vector of claim 7 further comprising a liver specific promoter.

9. The vector of claim 8, wherein the promoter is a hybrid liver-specific promoter (HLP).

10. The vector of claim 7, wherein the vector is a rAAV vector.

11. The vector of claim 7, wherein the vector is a single stranded vector.

12. A host cell comprising the nucleic acid molecule of claim 1 or the vector of claim 7.

13. A transgenic non-human animal comprising cells comprising the nucleic acid molecule of claim 1 or the vector of claim 7.

14. A pharmaceutical composition comprising the nucleic acid molecule of claim 1 or the vector of claim 7, and one or more pharmaceutically acceptable excipients.

15. A method of treating diabetes comprising:
administering a therapeutically effective amount of the vector of claim 7 to a patient suffering from diabetes.

16. A method for delivery of a nucleotide sequence encoding preproinsulin protein to a subject, which method comprises:
administering to the subject the nucleic acid molecule of claim 1 or the vector of claim 7.

* * * * *

SEQUENCE LISTING

```
<160> NUMBER OF SEQ ID NOS: 2

<210> SEQ ID NO 1
<211> LENGTH: 333
<212> TYPE: DNA
<213> ORGANISM: Artificial sequence
<220> FEATURE:
<223> OTHER INFORMATION: Nucleotide sequence of codon optimised insulin
      gene

<400> SEQUENCE: 1
atggctcttt ggatgagact gcttcctctg cttgctctgc tggccctctg gggacctgat     60
cctgctgctg cctttgtgaa tcagcatctg tgcggctccg atcttgtgga agctctgtat    120
cttgtgtgcg gagaaagagg cttttttac acacccagga cccgccggga agccgaagac    180
ctgcaggtgg ggcaggtgga gctgggaggc ggacctggag ccggcagcct gcagcccttg    240
```

```
gccctggagg ggtcccggca gaagcgtggc atcgtggaac agtgctgcac ctccatctgc    300
tccctgtatc agctggaaaa ttattgcaat tag                                 333
```

```
<210> SEQ ID NO 2
<211> LENGTH: 110
<212> TYPE: PRT
<213> ORGANISM: Homo sapiens

<400> SEQUENCE: 2

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser Asp Leu Val Glu Ala Leu Tyr Leu Val Cys Gly Glu Arg Gly Phe
        35                  40                  45

Phe Tyr Thr Pro Arg Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Arg Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110
```